United States Patent
Fu

(10) Patent No.: US 9,499,814 B2
(45) Date of Patent: Nov. 22, 2016

(54) METHODS FOR IDENTIFYING DRUG EFFECTS ON A CELL BY DETERMINING CHANGES IN THE CELL'S SPLICED MESSAGE PROFILE

(75) Inventor: Xiang-Dong Fu, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 27 days.

(21) Appl. No.: 13/574,090

(22) PCT Filed: Jan. 20, 2011

(86) PCT No.: PCT/US2011/021808
§ 371 (c)(1),
(2), (4) Date: Aug. 15, 2012

(87) PCT Pub. No.: WO2011/091106
PCT Pub. Date: Jul. 28, 2011

(65) Prior Publication Data
US 2012/0302451 A1    Nov. 29, 2012

Related U.S. Application Data

(60) Provisional application No. 61/297,492, filed on Jan. 22, 2010.

(51) Int. Cl.
  C12Q 1/68 (2006.01)
  C12N 15/11 (2006.01)
  C07H 21/04 (2006.01)

(52) U.S. Cl.
  CPC ........... *C12N 15/111* (2013.01); *C12Q 1/6809* (2013.01); *C12Q 1/6853* (2013.01); *C12Q 1/6862* (2013.01); *C12Q 1/6883* (2013.01); C12N 2310/11 (2013.01); C12N 2310/14 (2013.01); C12N 2310/141 (2013.01); C12N 2320/11 (2013.01); C12N 2320/12 (2013.01); C12Q 2600/136 (2013.01); C12Q 2600/158 (2013.01)

(58) Field of Classification Search
  None
  See application file for complete search history.

(56) References Cited

U.S. PATENT DOCUMENTS

| 6,027,889 A | 2/2000 | Barany et al. |
| 7,115,400 B1 * | 10/2006 | Adessi et al. ............... 435/91.2 |
| 2003/0003490 A1 | 1/2003 | Fan et al. |
| 2004/0137484 A1 * | 7/2004 | Zhang .................... C12Q 1/682 435/6.11 |
| 2007/0059703 A1 | 3/2007 | Fu et al. |
| 2010/0130373 A1 * | 5/2010 | Dekker .............. C12N 15/1093 506/9 |

FOREIGN PATENT DOCUMENTS

| WO | 9615271 A1 | 5/1996 | |
| WO | WO96/15271 * | 5/1996 | ............... C12Q 1/68 1/70 |
| WO | WO/2005/007814 * | 1/2005 | ............... C12N 9/00 |
| WO | 2008069906 A2 | 6/2008 | |

OTHER PUBLICATIONS

Braconi et al. "Candidate therapeutic agents for hepatocellular cancer can be identified from phenotype-associated gene expression signatures" (Cancer vol. 115, issue 16, pp. 3738-3748, published online Jun. 9, 2009.*
Lunn, Mitchell R;Wang, Ching H The Lancet; Jun. 21-Jun. 27, 2008; 371, 9630; ProQuest pg. 2120.*
Mercier et al. (Biophysical Journal 85(4) pp. 2075-2086).*
Fan et al. (Genome Research vol. 14, pp. 878-885, 2004).*
Semizarov & Blomme (Genomics in Drug Discovery and Development 2009 published by John Wiley & Sons, Inc., Hoboken, New Jersey).*
Cosma et al., "Ordered recruitment of transcription and chromatin remodeling factors to a cell cycle- and developmentally regulated promoter", Cell, Apr. 30, 1999, vol. 97, No. 3, pp. 299-311.
Cheon Myeong Sook, International Search Report and Written Opinion, PCT/US2011/021808, Korean Intellectual Property Office, Oct. 5, 2011.

* cited by examiner

*Primary Examiner* — Catherine S Hibbert
(74) *Attorney, Agent, or Firm* — Gavrilovich, Dodd & Lindsey LLP

(57) ABSTRACT

The invention provides products of manufacture for screening for compositions that can modify a cell's gene expression profile, and methods for making and using them. In one embodiment, the invention provides products of manufacture and methods comprising a high content, high throughput screening for a composition (e.g., chemicals, small molecules) that can modify a cell's physiology based on the composition's ability to modify the cell's gene expression signature.

14 Claims, 5 Drawing Sheets

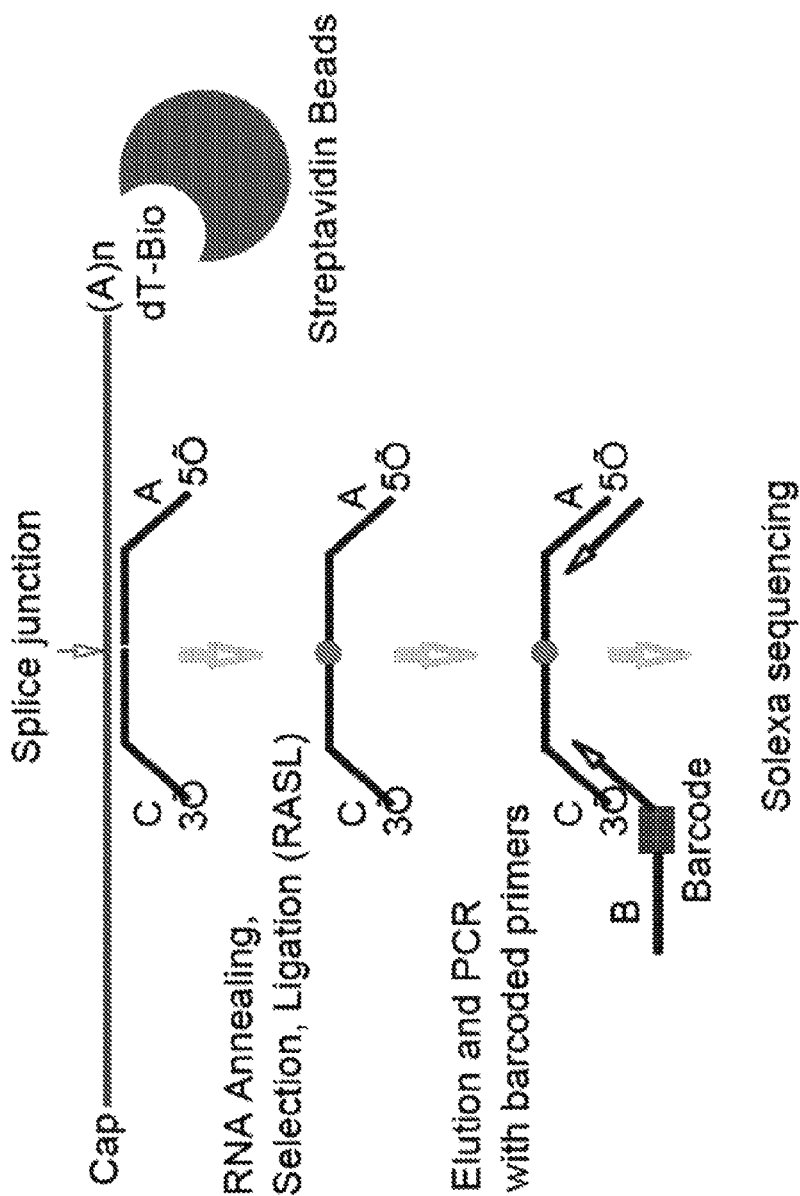
Figure 1. The RASL-seq technology

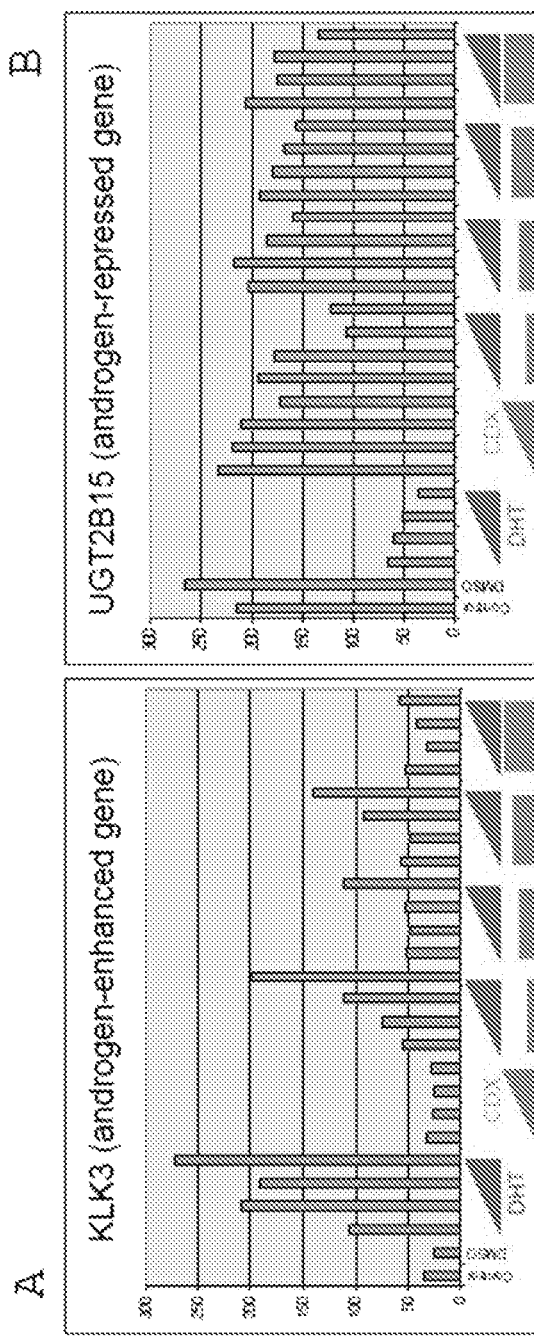
Figure 2. Examples of androgen (DHT, red gradients) induced and suppressed genes that are specific reversed by the androgen antagonist CDX (blue gradient). The results were obtained from multiplex RASL-seq analysis.

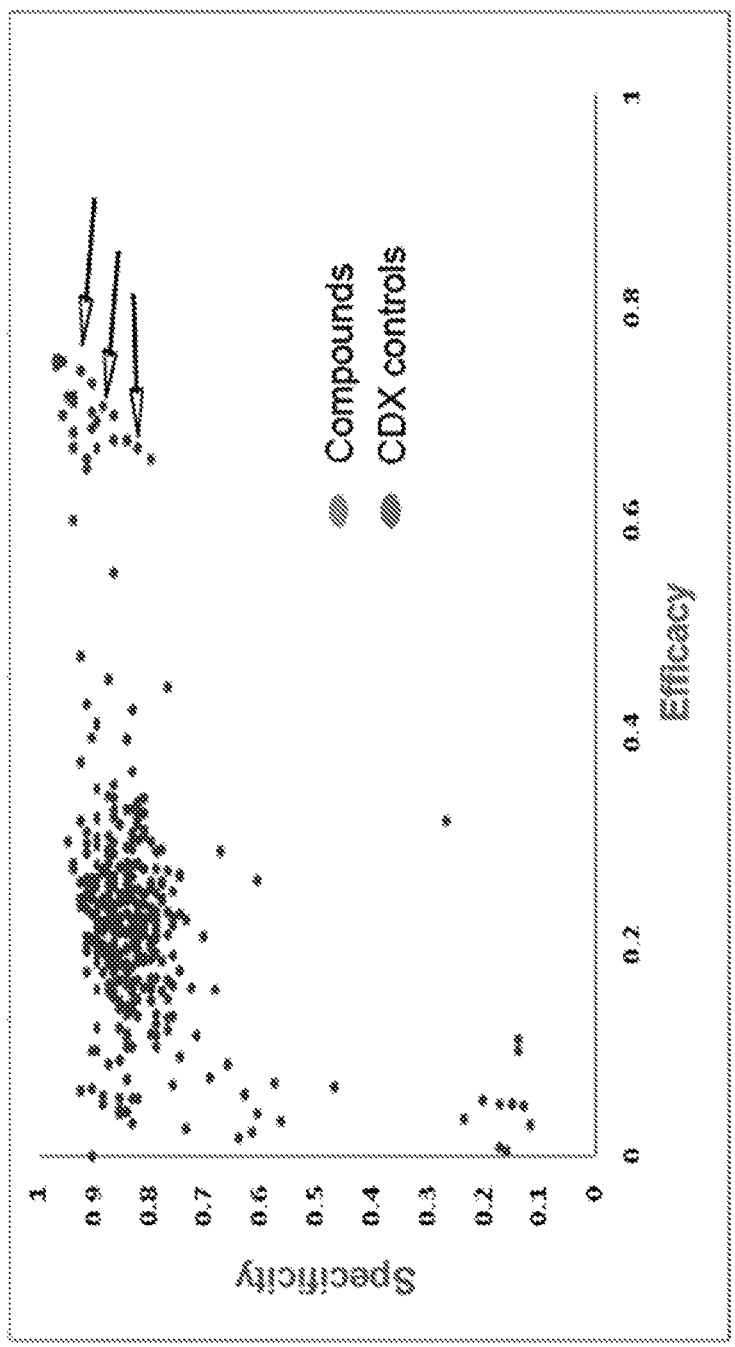
Figure 3. Preliminary screen for AR antagonists. The known AR antagonist CDX was tested in randomly selected wells as internal controls. Arrows: Candidate hits that show high specificity and efficacy scores.

Results of RASL-seq are highly reproducible and quantitative.

Quantitative inhibition of androgen response by Bicluamide. Effects on DHT-induced (KLK3, left) and suppressed (UGT2G15, right) are shown to illustrate dosage-dependent effect of Biclutamide as androgen (DHT) antagonist.

METHODS FOR IDENTIFYING DRUG EFFECTS ON A CELL BY DETERMINING CHANGES IN THE CELL'S SPLICED MESSAGE PROFILE

CROSS-REFERENCE TO RELATED APPLICATIONS

This United States utility patent application is the §371 national phase of PCT international patent application no. PCT/US2011/021808 having an international filing date of Jan. 20, 2011, which claims benefit of priority to U.S. Provisional Patent Application Ser. No. 61/297,492, filed Jan. 22, 2010. The aforementioned applications are expressly incorporated herein by reference in their entirety and for all purposes.

TECHNICAL FIELD

This invention generally relates to drug discovery and molecular biology. In particular, in alternative embodiments, the invention provides products of manufacture for screening for compositions that can modify a cell's gene expression profile, and methods for making and using them. In one embodiment, the invention provides products of manufacture and methods comprising a high content, high throughput screening for a composition (e.g., chemicals, small molecules) that can modify a cell's physiology based on the composition's ability to modify the cell's gene expression signature.

BACKGROUND

Current cell-based assays for drug discovery have many drawbacks, which make the process inefficient, costly or unapproachable when specific molecular targets remain undefined: genetic engineering is often required to develop a reporter cell line; most screens depend on a single or a limited number of surrogate readouts without capturing the information on broad and potential non-specific effects of candidate hits; toxic components are not filtered out at the early stages of screening; and/or many diseases lack "druggable" targets against which a screening strategy can be developed.

SUMMARY

In alternative embodiments, the invention provides compositions and methods for gene signature-based drug-screening, which can be practiced as high throughput applications. In alternative embodiments methods of the invention can be practiced without RNA isolation. In one exemplary procedure (method) of the invention, eliminating the tedious RNA isolation step facilitates the procedure's adaptation to a high throughput application, e.g., to a robotic operation.

In alternative embodiments, the invention provides methods for determining or measuring if a test compound or compounds or a putative drug composition(s) can modify or alter the physiology of a cell, comprising:
(i) determining the gene expression signature of a cell or cells, and
(ii) determining the gene expression signature of the same or equivalent cell or cells after:
(a) providing a test compound or compounds or a putative drug composition(s);
(b) providing a cell or cells (e.g., the same or equivalent cell or cells);
(c) culturing the test compound or compounds or the putative drug composition(s) of (a) with the cell or cells of (b); or contacting the test compound or compounds or the putative drug composition(s) of (a) with the cell or cells of (b); and
(d) determining or measuring a difference or change in the gene expression signature of the cell or cells based on a difference or change between the gene expression signature of the cell or cells not contacted or cultured with the test compound or compounds or the putative drug composition(s) with those that are contacted or cultured with the test compound or compounds or the putative drug composition(s), wherein a difference or change in the gene expression signature of the cell or cells between step (i) and step (ii), or a difference or change in the gene expression signature of the cell or cells after contacting or culturing the cells or cells with the test compound or compounds or putative drug composition(s), identifies the test compound or compounds or putative drug composition(s) as a composition or drug that can modify or alter the physiology of the cell;

and optionally step (i) and step (ii) are performed concurrently, or step (i) is performed before step (ii), or step (ii) is performed before step (i);

wherein the gene expression signature of the cell or cells is determined by a method comprising amplification of all or substantially all of the spliced RNA message (spliced mRNA) expressed in the cell or cells, or a selected subset of spliced RNA message (spliced mRNA) expressed in the cell or cells, and optionally sequencing the amplified RNA messages (mRNA), and amplification of all or substantially all or a subset of the spliced RNA message (spliced mRNA) in the cells or cells is by a method comprising:
(1) providing a plurality of oligonucleotide primer pairs (a first and a second primer),
wherein each primer pair (the first and the second primer) comprises a sequence designed to specifically hybridize (anneal) to a spliced message (mRNA) such that when the primer pair is hybridized (annealed) to one strand of the spliced mRNA the first and the second primers are sufficiently adjacent such that they can be ligated by an enzyme in the presence or absence of free nucleotides,
and optionally the enzyme is a ligase,
and optionally the ligase is a T4 kinase (e.g., for RNA-templated oligonucleotide ligation) or a Taq ligase (e.g., for a DNA-templated ligation),
and optionally the first and the second primers are directly adjacent to each other when specifically hybridized (annealed) to the spliced message (mRNA) to which they were designed to hybridize (anneal) to,
and one or both of the first primer and/or the second primer comprises a unique (e.g., "barcode") sequence that uniquely identifies that primer or primer pair from all the other plurality of primers or primer pairs,
and one or both of the first primer and/or the second primer comprises a capture moiety,
and optionally different primer pairs have different capture moieties,
and optionally the capture moiety comprises a biotin or an imino-biotin or equivalent;
(2) contacting and/or mixing the plurality of oligonucleotide primer pairs with:

a purified, semi-purified (partially purified) or unpurified (e.g., a cell lysate or a cell preparation not enriched for mRNA) cell lysate or cell preparation, or a plurality of cDNA molecules representative of the mRNA population of the cell or cells, or a cDNA library, under conditions wherein the plurality of oligonucleotide primer pairs can hybridize (anneal) to the mRNA in the cell lysate or cell preparation or the plurality of cDNA molecules or cDNA library;

(3) contacting and/or mixing the annealed plurality of oligonucleotide primer pairs and mRNA or cDNA with a ligase under conditions wherein the ligase can ligate the first and the second primer to each other;

(4) separating (e.g., substantially purifying or isolating) the plurality of ligated primer pairs from other components of the purified, semi-purified or unpurified cell preparation, or cDNA preparation or cDNA library, by contacting the plurality of ligated primer pairs with one or more binding partner(s) designed to specifically bind to ("capture") the one or more capture moieties, and optionally the binding partner is a streptavidin or equivalent, and optionally the binding partner is bound or linked to a bead or a platform, and optionally the platform comprises a SOLEXA™ platform (e.g., GENOME ANALYZER$_{IIe}$™ (Illumina Inc., San Diego, Calif.)) or a 454 SEQUENCING™ platform (454 Life Sciences Inc., Roche Applied Science, Branford, Conn.) platform;

(5) amplifying the separated or substantially purified or isolated plurality of ligated primer pairs, and optionally the amplification is by a method comprising polymerase chain reaction (PCR); and (6) identifying the presence of absence of, and/or the amount of, each specie of amplified, ligated primer pair, and optionally each specie of amplified, ligated primer pair is identified by sequencing or by hybridization (annealing) to a chip, a microassay, or a biochip, and optionally the sequencing is by a high-throughput sequencing, or dye-termination electrophoretic sequencing, or a microfluidic Sanger sequencing.

In alternative embodiments of the methods of the invention, the plurality of primer pairs are designed to specifically hybridize (anneal) to a plurality of spliced messages (mRNAs) that when expressed in a particular pattern or set represent a particular physiologic state of the cell, and optionally a subset of the plurality of primer pairs are designed to specifically hybridize (anneal) to a pattern or set or subset of spliced messages (mRNAs) that are expressed by housekeeping or constitutively expressed genes, and optionally a subset of the plurality of primer pairs are designed to specifically hybridize (anneal) to a set or subset of spliced messages (mRNAs) that represent a cell in a particular state of health, growth, senescence, pathology, toxicity response, apoptosis and/or stress;

and optionally a subset of the plurality of primer pairs are designed to specifically hybridize (anneal) to a set or subset of spliced messages (mRNAs) that identify the cell as a cancer cell, a cancer stem cell, a stem cell, a pluripotent cell, a particular normal or abnormal differentiated cell or a particular normal or abnormal undifferentiated cell.

In alternative embodiments of the methods of the invention, the test compound or compounds or the putative drug composition(s) comprises a library of compositions or compounds. The test compound or compounds or a putative drug composition(s) or the library of compositions can comprise a small molecule; a peptide, polypeptide or peptidomimetic; a nucleic acid or a natural or synthetic nucleotide; an antisense, an miRNA or an siRNA molecule; a polysaccharide or carbohydrate; and/or a lipid or a fat; or any combination thereof.

In alternative embodiments of the methods of the invention the cell or cells are contacted or cultured with the test compound or compounds or putative drug composition(s) or library of compositions before, during and/or after exposure of the cell or cells to a differentiation factor, a known carcinogen, a mutating agent, a histone modifying agent, an enzyme, a miRNA, an siRNA, a histone methyl-transferase, a demethylase, and/or an epigenetic factor.

In alternative embodiments the invention provides multiplexed systems comprising all the components needed to practice a method of the invention.

In alternative embodiments the invention provides kits comprising all the components needed to practice a method of the invention.

In alternative embodiments the invention provides uses of the multiplexed system to identify a putative drug to treat or ameliorate a pathology or a condition, or to induce a differentiation or de-differentiation of a cell, or to identify a cell in a particular state of health, growth, senescence, pathology, toxicity response, apoptosis and/or stress. In alternative embodiments the multiplexed systems can be used to identify a putative drug to treat or ameliorate an RNA-based disease or a disease based on or caused by, or exacerbated by, an RNA splicing event, e.g., an abnormal (e.g., not wild type) RNA splicing event. In alternative embodiments the RNA-based disease is a type 1 Myotonic Dystrophy (DM1) or spinal muscular atrophy (SMA).

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The drawings set forth herein are illustrative of embodiments of the invention and are not meant to limit the scope of the invention as encompassed by the claims.

FIG. 1 schematically illustrates an exemplary "RASL/DASL technology" that can be used to practice the high throughput methods of this invention, which can in alternative embodiments quantitatively measure alternative pre-mRNA splicing, as described in detail, below.

FIGS. 2A and 2B graphically illustrate data demonstrating the efficacy of an exemplary multiplex RASL-seq screening method of this invention where a known AR antagonist was used as a drug standard, as discussed in detail below.

FIG. 3 graphically illustrates data demonstrating the efficacy of an exemplary screening method of this invention, as discussed in detail below.

Like reference symbols in the various drawings indicate like elements.

Figures 4A, 4B:
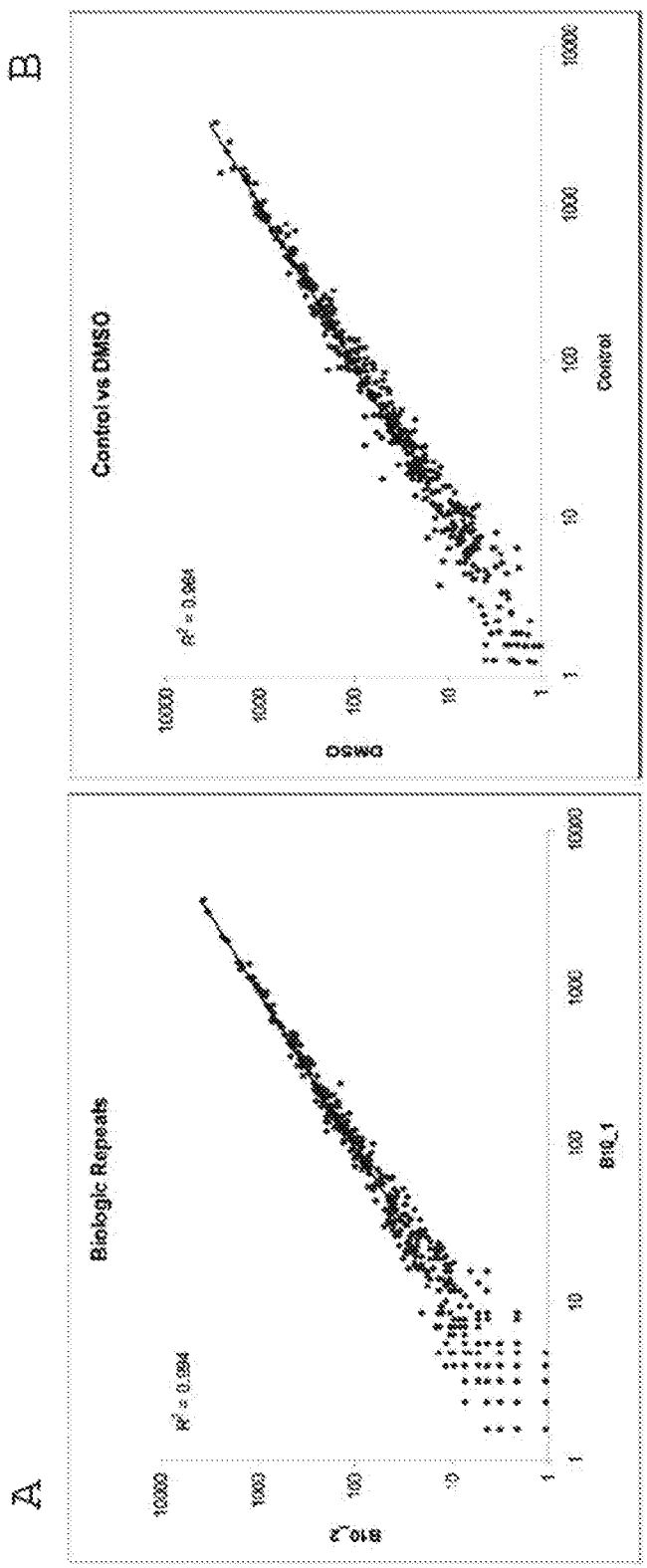
FIGS. 4A and 4B graphically illustrate data demonstrating that an exemplary sequence methodology used to practice this invention gives reproducible and quantitative results, as discussed in detail below.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In one embodiment, the invention provides compositions and methods for high content, high throughput chemical, e.g., drug, screening based on detection of a cell's "gene signature"—or gene expression profiling. In one embodiment, the invention uses one or more panel(s) of nucleic acid sequences representing specific genes, e.g., up to 500 or more, that represent the key differences between the beginning and the desirable end stage of a cell type or cell state (as a physiologic or developmental state) as a functional readout of the cell type or state (by detecting the expression of those genes in a cell). In one embodiment the methods use these panels of nucleic acid sequences to screen for chemicals or drugs that have a maximal intended effect but minimal side effect (by detecting a change in expression of those genes in a cell when the cell is exposed to the chemical or drug). In one embodiment a panel of sequences representing house-keeping and/or toxicity genes is also used as a control. In one embodiment the procedure comprises use of high throughput sequencing to detect the presence and/or change in expression of those genes in a cell.

This invention's use of "gene signature" or gene expression profiling distinguishes it from other cell-based assays in that in some embodiments it is based on a limited number of measurable parameters. In some embodiments this invention also eliminates the need to define specific targets for screening, and thus has wide applications.

In one embodiment the methods of the invention comprise a robotic chemical genetics system to identify small molecules for cell pathway dissection. Assays of the invention also can be used in various large-scale gene expression profiling experiments. For industry, assays of the invention can allow drug screening on previous non-druggable targets. Assays of the invention also can significantly shorten a screening process by having a series of controls to serve as counter-screens in the same assay. Assays of the invention can serve as the basis for modifications so that the technology can be adapted to many applications based on "gene signature".

In one aspect, the methods of the invention provide a systems biology approach that integrates chemical genetics, functional genomics and proteomics, bioinformatics and biochemistry. In one embodiment, the invention provides a technology platform that allows efficient genome-wide retrieval of gene signatures to serve as molecular indicators of functional states of cells. In one embodiment, "gene signatures", or gene expression profiles, are used as readouts for high throughput chemical screens, which would allow rapid discovery of novel chemical compounds, e.g., that could be drug candidates.

In one embodiment, the methods use a specially engineered chemical library to couple the chemical screens with biochemical and proteomics approaches to identify direct protein targets, thus shedding light on the underlying molecular mechanism of newly identified chemicals.

While the invention is not base on any particular mechanism of action, in one embodiment compositions and methods of the invention utilize a gene signature-based approach. For example, in one aspect, because each type of human cell is likely to have a unique spectrum of expressed genes, the profiling of such a gene expression signature by methods of this invention can provide a "finger print" for the functional state of that cell. Also, because unique sets of genes can characterize the cellular state associated with specific developmental stages or diseases, gene expression profiling, or "gene signature-based screening" by methods of the invention can characterize a cellular state associated with a specific developmental stage, physiologic state (e.g., stress), phenotype, disease or condition. In alternative embodiments, methods of the invention utilize a small panel of signature genes. This is often sufficient to define a specific cellular state(s) for a disease diagnosis and/or prognosis; see e.g. Liu et al., N Eng J Med 356:217, 2007. In alternative embodiments, methods of the invention are used to determine gene expression signatures that reflect different functional states of a cell and use these molecular signatures as readouts for the identification of compositions (e.g., potential drugs or differentiation agents), e.g., small molecules, proteins, and the like, capable of inducing switches from one functional state to another or to one phenotype or stage of differentiation to another.

In alternative embodiments, methods of the invention can overcome some of the major drawbacks associated with current cell-based assays: no cellular engineering are required and primary cells may be directly used for screening. In alternative embodiments, the results are based on multiple functional readouts; e.g., the specificity and potential cellular toxicity of a tested composition (e.g., putative drug) could be simultaneously evaluated by using a sizable panel of built-in controls such as housekeeping genes and toxicity related genes. In alternative embodiments, methods of the invention are equally applicable to druggable and non-druggable targets or to some diseases where specific targets remain undefined. Even with complex diseases that may result from combinatorial molecular defects, by using the methods of the invention it is possible to identify small molecules that have partial, but specific effects, and such hits can be subsequently tested in various combinations. The signature-based screening methods of the invention can be an efficient, cost-effective and high throughput.

RASL/DASL Strategy

In some embodiments, to determine a cell's "gene signature" the methods and compositions of the invention use a "RASL/DASL technology", which is a high throughput method to quantitatively measure alternative pre-mRNA splicing; e.g., as described in WO/2008/069906, Xiang-Dong Fu, et al; Yeakley et al., Nature Biotech. 20:353, 2002; Fan et al. (2004) Genome Res. 14:878; Li et al. (2006) Cancer Res. 66:4079.

In some embodiments, the RASL/DASL technology used to practice this invention comprises use of two specific oligonucleotides (oligos) to target a region of interest in a genomic DNA or a transcribed RNA, see the schematic of FIG. 1, below. In this exemplary embodiment, each oligo is flanked by a specific primer sequence for PCR. If a pair of oligos land on the intended target, they can be ligated to produce a PCR amplicon. Thus, this exemplary embodiment takes the advantage of the specificity of DNA ligase to control the specificity in oligo hybridization. In alternative embodiments, methods of the invention also comprise use of solid phase selection to enrich paired oligos on intended targets and to immobilize singleton oligos hybridized to illegitimate templates (thereby preventing their random collisions and ligation, which frequently occur when assays were carried out in solution).

In alternative embodiments, methods of the invention also comprise use of oligos where each pair is linked to a specific "zipcode" sequence (which can be about 20 nt in length) so that the final PCR products can be detected and quantified on a zipcode array. The ability to multiplex this assay with >20,000 pairs of oligos in a single reaction and used the technology to address some key biological questions on epigenetic control of gene expression as been demonstrated, see e.g., Kwon et al. (2007) Proc. Natl. Acad. Sci. 104:4852; Garcia-Bassets et al., Cell (2007) 128:505.

In alternative embodiments, methods of the invention adapt RASL for high throughput applications by, e.g.: establishing conditions to permit the RASL assay directly on cell lysate; incorporated use of a barcode strategy for multiplex sequencing of the RASL products on a SOLEXA™ platform (Illumina, San Diego, Calif.); and designated this exemplary embodiment "RASL-seq".

In alternative embodiments, to avoid potential interference by genomic DNA, we have designed individual oligo pairs against specific splice junction sequences so that they can only be paired on spliced mRNAs.

In alternative embodiments, cells are cultured in individual wells of microtiter plates. After drug/compound treatment, the cells are directly lysed and mixed with the oligo pool plus biotinylated oligo-dT as schematically diagrammed in FIG. 1, above. After annealing, streptavidin beads are used to capture oligo-dT, which in turn captures poly(A+) mRNA as well as specific oligo pairs on the mRNA. After this solid phase selection and buffer exchange, oligo pairs templated specifically by mRNA are ligated, converting only correctly paired oligos to full amplicons. The products from individual wells are next amplified using a set of bar-coded PCR primers that can be pooled for high throughput sequencing, e.g., on the SOLEXA™ system. By sequencing individual ligated oligos, the methods of the invention can determine the levels of specifically targeted mRNAs, and by sequencing the bar-codes, methods of the invention can identify individual biological samples from the pool.

Our data demonstrated that a single, specific oligo pair against a specific mRNA is sufficient to give the quantitative information in such multiplex assay. We demonstrated that the methods of the invention have sufficient sensitivity to work on cells cultured in 384 plates. We determined by using methods of the invention that a single SOLEXA™ run is sufficient to quantitatively profile approximately 400 genes from 8×384=approximately 3000 samples, which currently costs about $2 per sample compared to about $100 per sample for the zipcode array method.

The invention also provides exemplary assays that it can be readily adapted to a robotic operation. Therefore, exemplary screening platforms of the invention have fulfilled several key requirements for large-scale drug screening in terms of sensitivity, specificity, high throughput, cost-efficiency, and the ability for automation.

Proof-of-Concept Experiments on a Prostate Cancer Model:

To demonstrate the feasibility of the signature-based strategy, we have conducted a preliminary drug screening using an exemplary method of this invention to identify small molecules that can specifically antagonize the function of the androgen receptor (AR) in LNCaP cells. For this purpose, we performed genome-wide RNA-seq and identified a panel of signature androgen-responsive genes. We selected about 200 androgen-responsive, AR-dependent genes (both up- and down-regulated) for functional readouts and about 100 housekeeping genes and about 100 toxicity-related genes for specificity and cellular toxicity controls. A known AR antagonist bicalutamide (known as CDX, is a non-steriodal Androgen Receptor (AR) antagonist and a pure anti-androgen) was used as a drug standard, which indeed showed the specific effect on both androgen up- and down-regulated genes, as illustrated on two specific androgen-regulated genes from a multiplex RASL-seq experiment; data is graphically illustrated in FIG. 2, below. FIG. 2A (KLK3, androgen enhanced gene) and FIG. 2B (UGT2B15, androgen-repressed gene) graphically illustrate example of androgen (DHT, red gradients) induced and suppressed genes that are specifically reversed by the androgen antagonist CDX (blue gradient). The results were obtained from multiplex RASL-seq analysis.

To perform a proof-of-concept experiment, we selected a collection of FDA-approved drugs consisting of about 3000 compounds and asked whether any existing, clinically tested drug(s) is able to suppress androgen-induced gene expression specifically, yet exhibit minimal impact on housekeeping and toxicity-related genes. We have developed vectorial component scoring system for each compound. The Efficacy (EF) score measures the effect on androgen-regulated genes, which ranges from 1 to −1, with 1 indicative of a full effect (i.e. all androgen-up regulated genes are suppressed and all androgen down-regulated genes are derepressed), 0 indicative of no effect, and −1 indicative of the agonist effect. The Specificity (SP) score determines the selective effect in the range of 1 to 0, with 1 indicative of no effect on the housekeeping genes and 0 indicative of non-specific effects on these genes (i.e. all housekeeping genes are non-specifically up- or down-regulated). We can similarly assign a Toxicity score for each compound.

Importantly, our preliminary screen revealed that all randomly placed CDX controls exhibited high EF and SP scores based on the current scoring system, as graphically illustrated in FIG. 3, below. FIG. 3 illustrates a preliminary screen for AR antagonists. The known AR antagonist CDX was tested in randomly selected wells as internal controls. Arrows illustrate (indicate) candidate hits that show high specificity and efficacy scores.

Interestingly, we also identified a number of candidate hits that appear to have similar effects to CDX (arrows in FIG. 3). These experiments have thus demonstrated the feasibility of exemplary methods of this invention (incorporating RASL-seq technology) for signature-based drug screening. The Chemical Genetic Approach to Basic and Translational Research:

In alternative embodiments, the invention uses a systems biology approach to become a broadly applicable drug discovery program. In alternative embodiments, methods of the invention are used to develop therapeutics against specific cancers and (other) RNA-based diseases. In one embodiment, the methods of the invention are practiced using a 3000 compound collection developed on the prostate cancer model; or with a library of 100,000 compounds representing 34 distinct structure scaffolds (which has successfully yielded multiple drug leads); see e.g., Ding et al., (2003) Proc. Natl. Acad. Sci. 100:7632.

In one embodiment, the methods of the invention are partially or completely automated, e.g., the entire RASL procedure is automated, e.g., on a Beckman robotic system. In alternative screening embodiments, methods can initially screen a 3K compound library and then a 100K library. Drug leads can be subjected to structure-activity-relationship (SAR) studies based on 2D chemical structure and/or 3D pharmacophore using existing computational chemistry methods. Additional derivatives of initial hits can be prepared to further explore SAR.

In one embodiment, a chemical library is converted to affinity resins to identify compounds for target protein identification by mass-spec and mechanistic studies, e.g., as described by Chen et al., Proc. Natl. Acad. Sci. (2006) 103:17266; Zhang et al. (2007) Proc. Natl. Acad. Sci. 104:7444. In alternative embodiments, methods of the invention have broad applications in both basic and translational research.

Use RASL-seq to Address Critical Problems in Cancer Genetics

In alternative embodiments, methods of the invention use knowledge of regulated gene expression in prostate and breast cancer cells to screen for putative therapeutic and prophylactic drug candidates. Methods of the invention can be used to address problems in prostate cancer research, for example, the advance of primary tumors to androgen resistance characterized by androgen-independent, but the androgen receptor-dependent growth. This is largely responsible for patient mortality. All existing therapeutics based on androgen antagonists fail on androgen-resistant prostate cancer. Thus, exemplary methods of the invention can be used to identify small molecules that can act beyond ligand binding.

LNCaP, which is androgen-sensitive, and its derivative LNCaP-C4-2B, which became androgen resistant; see e.g., Wu et al., Int J Cancer 57:406, 1994, can be used as a cellular model to profile AR-dependent genes by a method of this invention, e.g., incorporating RNA-seq, to identify a key "gene signature" and an effective (candidate) drug for both cell types. CDX will be used as a control and for comparison with candidate hits.

In one aspect, methods of this invention can provide hits capable of blocking AR-dependent gene expression in both androgen-sensitive and resistant cells, the latter of which should show no response to CDX. Candidate (putative drug) hits can be further tested on multiple pairs of androgen sensitive and resistant xenografts as described e.g., by Chen et al., Nature Med. 10:33, 2004.

Putative drug compounds also can be analyzed by methods of this invention incorporating e.g., RNA-seq and/or ChIP-seq to determine their impact genome-wide on AR-mediated gene expression and then characterized by a series of assays to determine their action points in the AR pathway, including the localization of the AR (cytoplasmic vs. nuclear by immunochemistry), AR binding on genomic targets (by ChIP), AR-dependent recruitment of key co-activators, such as Tip60, and AR-dependent displacement of key co-repressors, such as TBL1 and NcoR (by ChIP).

Besides these mechanistic studies, methods of this invention also can be used to determine the effect of compound (putative drug) leads on cell growth, migration, and metastasis. Some of these key assays also can be performed on drug derivatives during SAR analysis.

This exemplary method of the invention, as used with a prostate cancer model, also is clearly applicable to other cancer types. In one embodiment, a breast cancer model is also used, e.g., for breast cancer metastasis, see e.g., Yang and Weinberg, Dev Cell 14:818, 2008. Exemplary methods of the invention can identify key signatures regulated by breast cancer cells transcription factors, e.g., in MDA-MB-453 breast cancer cells, and screen for small molecules that can selectively suppress the transcription program induced by each of these factors. Drug leads will be tested for their effects on the epithelial-mesenchymal transition (EMT) in addition to an array of tumor metastasis assays as described e.g., by Yang et al., Cell 117:927, 2004.

Exemplary methods of the invention also can identify specific epigenetic controls, e.g., inhibitors to histone methyl-transferases and demethylases, e.g., as described by Kouzarides T, Cell 128:693, 2007, and other epigenetic controls which have been linked to many types of cancer. Cancer genetics is tightly linked to epigenetic control of gene expression. For example, it has been demonstrated that an altered balance between H3K9 methylation and demethylation triggered estrogen receptor-dependent gene expression in the absence of ligand; see e.g., Garcia-Bassets et al., Cell 128:505, 2007.

Exemplary methods of the invention can identify compositions that have the ability to intervene in specific epigenetic pathways; these compositions may hold a key to cancer therapeutics. In one embodiment, the invention comprises use of a signature-based screening method of the invention coupled with systematic RNAi to identify compositions that have the ability to intervene in specific epigenetic pathways.

For example, in one exemplary embodiment—briefly, a multiplex RNA-seq strategy of the invention is used to profile MCF7 and LNCaP cells before and after RNAi against individual histone modifying enzymes to identify a signature capable of differentiating multiple RNAi effects and then chemical screens are conducted to identify small molecules that mimic some specific effects of RNAi. Because chemical inhibition is unlikely to fully capture the knockdown effect in most cases, particular attention is given to partial, but specific effects. Candidate hits can be further characterized at the genome-wide level by the RNA-seq methods of the invention, as well as at the biochemical levels by using purified enzymes. Epigenetic signatures can be used with methods of this invention to conduct genome-wide RNAi. This can decipher many critical pathways in regulated gene expression, e.g., as recently demonstrated on the dendritic cell model by e.g., Amit et al., Science online, 2009. By combining these systems biology approaches with methods of this invention, drug actions can be linked to specific pathways.

In one embodiment, the signature-based drug-screening platform of this invention is practiced as a high throughput application; and in alternative embodiments methods of the invention can be practiced without RNA isolation; eliminating the tedious RNA isolation step in one exemplary procedure of the invention facilitates its adaptation to a robotic operation.

In one embodiment, this is accomplished by direct cell lysis and RNA capture in a single step. In one embodiment, an oligo-dT primer is immobilized on beads, which captures mRNA and the mRNA captures target-specific oligo pairs. This permits all following assays in the solid phase. Upon RNA-mediated oligo ligation by T4 kinase, all specific oligo pairs are converted to PCR amplicons, which carry out universal primers on both ends for PCR amplification and subsequent sequencing on the SOLEXA™ platform genome analyzer. In one embodiment, to take advantage of high-density reading, the invention uses a massive multiplex strategy using bar-coded primers for each PCR reaction. This allows pooling of PCR reactions from multiple well plates, e.g., 96 or 384 wells, for multiplex sequencing. As illustrated in FIG. 4, this embodiment gives highly reproducible digital readouts. FIGS. 4A and 4B graphically illustrate the results of the RASL-seq protocol of the invention is highly reproducible and quantitative; FIG. 4A is the biologic repeat sample, and FIG. 4B is the control vs DMSO sample.

Figures 5A, 5B:
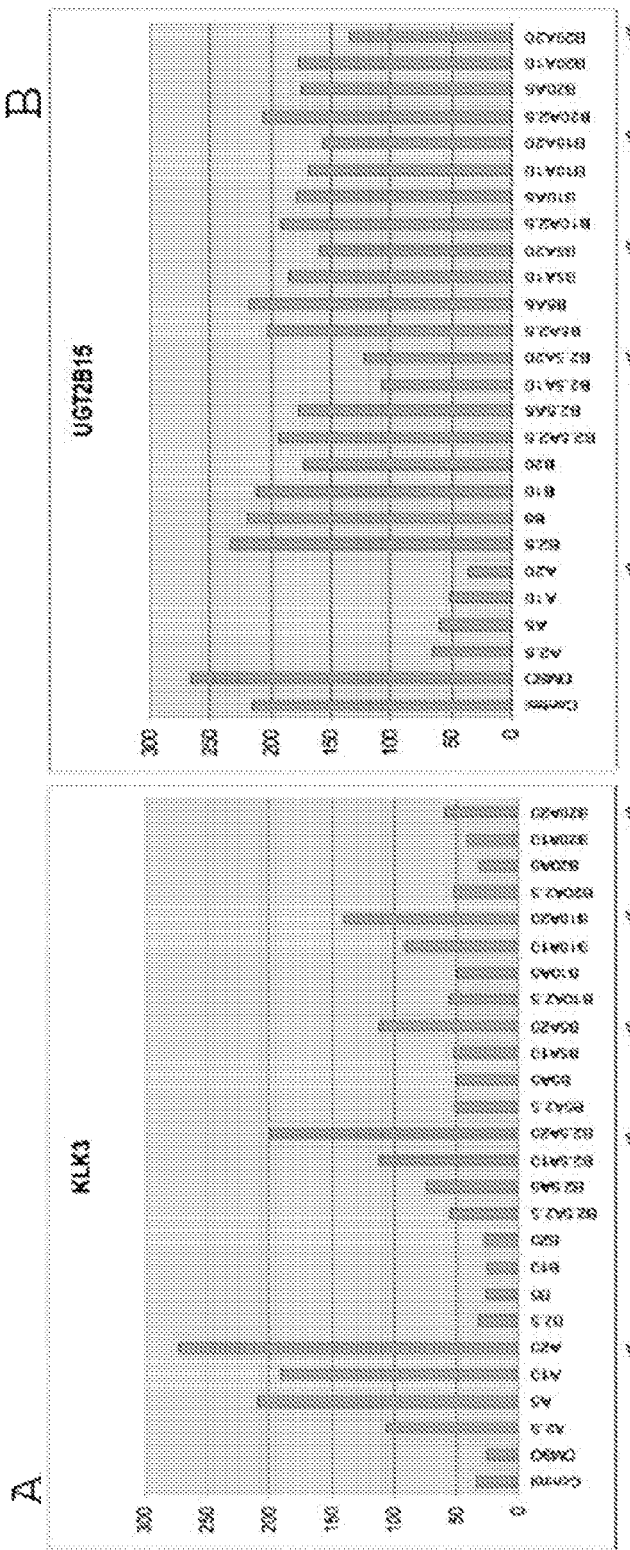
FIGS. 5A and 5B graphically illustrate data demonstrating the efficacy of an exemplary screening method of this invention, as discussed in detail below.

As illustrated in FIG. 5, we further demonstrated that we are able to robustly score androgen-induced gene expression in LNCaP cells in and the anti-androgen effect by the established drugs, such as biclutamide (CDX). FIGS. 5A and 5B graphically illustrate quantitative inhibition of androgen response by biclutamide. Effects on DHT-induced (KLK3, left, FIG. 5A) and suppressed (UGT2G15, right, FIG. 5B) are shown to illustrate the dosage-dependent effect of bicalutamide as an androgen (DHT) antagonist.

Use the New Technology Platform to Attack RNA-Based Diseases:

In alternative embodiments, methods of this invention are used to screen for compositions, e.g., putative drugs, that can modify or regulate splicing in development and disease, e.g. RNA-based diseases.

For example, in one embodiment, methods of this invention are used to screen for the RNA disease type 1 Myotonic Dystrophy (DM1) caused by expanded CUG or CCUG repeats, resulting in sequestration by the RNA binding protein Muscleblind (MBNL) in the nucleus, e.g., as described by Wheeler and Thornton, Curr Opin Neurol 20:572, 2007. There are two MBNL genes, MBNL1 and MBNL2, in mammals, but the phenotype appears to be largely mediated by MBNL1 as null mutation of this gene is sufficient to recapture the muscle waste phenotype in mice (see, e.g., Kanadia et al., Science 302:1978, 2003). Recent analysis of MBNL1 null mice revealed a large number of altered RNA splicing events that were similarly detected in DM1 patients. One of the major targets for MBNL1 is the chloride channel ClC-1 gene whose splicing defect has been linked to defective muscle relaxation (see, e.g., Charlet et al., Mol Cell 10:45, 2002). In one embodiment, methods of this invention are used to screen for compositions, e.g., putative drugs, that can modify or regulate altered splicing events that can individually or collectively contribute to a disease phenotype. In one embodiment, methods of this invention are used to screen for compositions, e.g., small molecules as putative drugs, that can specifically reverse many of the altered (pathology-inducing) splicing events. In one embodiment, methods of this invention are used to screen for compositions that can inhibit splicing repressors. In one embodiment, methods of this invention are used to screen for compositions, e.g., small molecules, that can switch specific alternative splicing events in report assays; see e.g. Soilov et al., Proc. Natl. Acad. Sci. 105:11218, 2008; O'Brien et al., JCB 283:33147, 2008.

In one embodiment, methods of this invention use splicing arrays to screen for compositions, e.g., small molecules as putative drugs, that can specifically reverse splicing defects, e.g., in DM1 using. The MEFs derived from MBNL1 null mice exhibited similar splicing defects as in DM1 patients, suggesting that the MEFs could be used as a surrogate cellular system for defective muscle in our screen.

On exemplary method comprises use of a panel of RASL oligos to interrogate about 120 splicing events reliably detected by the splicing array. An equal number of other alternative splicing events can be similarly targeted as specificity controls. Lead compounds can be characterized by comparing their differential effects between wild type and the mutant MEFs. Pre-clinical tests can be carried out on MBNL1 null and CUG-expanded mouse models.

In one embodiment, methods of this invention are used to screen for compositions, e.g., putative drugs, that can modify or regulate (treat or ameliorate) spinal muscular atrophy (SMA), which has been linked to the defective SMN1 gene functioning in snRNP recycling. The human genome also carries the SMN2 gene, which provides a partial (about 20%) function of SMN1 due to inefficient exon 7 inclusion caused by a point mutation in the exon. In one embodiment, methods of this invention are used to screen for compositions, e.g., putative drugs, that can enhance SMN2 splicing. In one embodiment, methods of this invention are used to screen for compositions, e.g., putative drugs, that can specifically reverse SMA-induced splicing events.

In one embodiment, methods of this invention are used to screen for compositions, e.g., putative drugs, that can modify or regulate (treat or ameliorate) motor neuron disease ALS, which has been linked to SOD1 (see, e.g., Bruijn et al., Science 281:1851, 1998), and more recently, to two RNA binding proteins TDP-43 (see, e.g., Sreedharan et al., Science 319:1668, 2008) and TLS (see, e.g., Kwiatkowski et al., Science 323:1205, 2009).

Thus, in alternative embodiments, methods of this invention comprise use of an appropriate cellular model to identify specifically altered splicing events, and screen for small molecules capable of specifically reversing the splicing signature without major side effects on other splicing events built in our assays as controls.

Products of Manufacture, Kits

The invention also provides products of manufacture, kits and multiplexed systems for practicing the methods of this invention. In alternative embodiments, the invention provides products of manufacture, kits and/or multiplexed systems comprising all the components needed to practice a method of the invention.

The invention will be further described with reference to the examples described herein; however, it is to be understood that the invention is not limited to such examples.

A number of embodiments of the invention have been described. Nevertheless, it will be understood that various modifications may be made without departing from the spirit and scope of the invention. Accordingly, other embodiments are within the scope of the following claims.

What is claimed is:

1. A method for determining whether a test compound modifies or alters gene expression in a cell, comprising:
    (a) identifying a gene signature comprising a plurality of genes associated with differences between the beginning and an end stage of a cell type;
    (b) obtaining mRNA from a control cell not contacted with the test compound;
    (b1) contacting a test cell with the test compound;
    (c) obtaining mRNA from the cell that has been contacted with the test compound;
    (d) contacting the mRNA from (b) and (c) with an oligo-dT linked to a capture moiety to obtain capture-tagged mRNA;
    (e) contacting the capture-tagged mRNA with a plurality of oligonucleotide pairs that anneal to the plurality of genes, each of the oligonucleotides of the pair of oligonucleotides having a sequence designed to specifically hybridize or anneal to an mRNA message of the plurality of genes such that when both the first and second primer of the primer pair are hybridized or annealed to the mRNA, the first and the second primers can be ligated and wherein the oligonucleotide pairs comprise a sequence complementary to a bar-coded PCR primer;
    (f) capturing the capture-tagged mRNA comprising annealed oligonucleotide pairs on a solid phase;

(g) washing the captured mRNA;
(h) ligating adjacent oligonucleotide pairs;
(i) denaturing and eluting ligated oligonucleotide pairs;
(j) amplifying the ligated oligonucleotide pairs with the bar-coded PCR primer to obtain bar-coded amplicons;
(k) sequencing the bar-coded amplicons to obtain sequence information; and
(l) determining a difference in the gene signature between the cell not contacted with the test compound compared to the cell contacted with the test compound using the sequence information,
wherein finding a difference in the gene signature is indicative of a test compound the modifies gene expression in the cell.

2. The method of claim 1, wherein the test compound comprises a library of compositions or compounds.

3. The method of claim 1, wherein the test compound comprises a small molecule, a peptide, a polypeptide, a peptidomimetic, a nucleic acid, a polysaccharide or carbohydrate; and/or a lipid or a fat.

4. The method of claim 3, wherein the nucleic acid is an antisense, an miRNA or an siRNA molecule.

5. The method of claim 1, wherein the cell is contacted with the test compound before, during and/or after exposure of the cell to a differentiation factor, a carcinogen, a mutating agent, a histone modifying agent, an enzyme, a miRNA, an siRNA, a histone methyl-transferase, a demethylase, and/or an epigenetic factor.

6. The method of claim 1, wherein the sequence complementary to a bar-coded PCR primer is a universal primer sequence.

7. The method of claim 1, wherein the bar-coded primer is different between the cell not contacted with the test compound and the cell contacted with the compound.

8. The method of claim 1, wherein the capture moiety and capturing is by biotin-streptavidin.

9. The method of claim 1, wherein the solid phase is a bead or a platform.

10. The method of claim 1, wherein a subset of the plurality genes are housekeeping or constitutively expressed genes.

11. The method of claim 1, wherein the oligonucleotide pairs hybridize to spliced mRNA.

12. The method of claim 1, wherein the beginning and end stage of the cell comprise a stem cell and a differentiated cell.

13. The method of claim 1, wherein the beginning and end stage of the cell comprise a normal cell and a cancer cell.

14. The method of claim 1, wherein the capture moiety comprises a biotin or an imino-biotin or equivalent.

* * * * *